United States Patent [19]

Reissenweber et al.

[11] Patent Number: 5,310,915
[45] Date of Patent: May 10, 1994

[54] PROCESS FOR THE PURIFICATION OF 7-CHLOROQUINOLINE-8-CARBOXYLIC ACIDS

[75] Inventors: Gernot Reissenweber, Boehl-Iggelheim; Knut Koob, Mutterstadt; Winfried Richarz, Stockstadt, all of Fed. Rep. of Germany

[73] Assignee: BASF Aktiengesellschaft, Ludwigshafen, Fed. Rep. of Germany

[21] Appl. No.: 915,992

[22] PCT Filed: Jan. 25, 1991

[86] PCT No.: PCT/EP91/00143
  § 371 Date: Aug. 3, 1992
  § 102(e) Date: Aug. 3, 1992

[87] PCT Pub. No.: WO91/11436
  PCT Pub. Date: Aug. 8, 1991

[30] Foreign Application Priority Data

Feb. 3, 1990 [DE]  Fed. Rep. of Germany ....... 4003174

[51] Int. Cl.$^5$ ............................................. C07D 215/10
[52] U.S. Cl. ..................................... 546/168; 546/170
[58] Field of Search ............................... 546/170, 168

[56] References Cited

U.S. PATENT DOCUMENTS

| | | | |
|---|---|---|---|
| 4,497,651 | 2/1985 | Hagen | 71/94 |
| 4,632,696 | 12/1986 | Hagen | 71/94 |
| 4,845,226 | 7/1989 | Hagen et al. | 546/180 |

FOREIGN PATENT DOCUMENTS

| | | |
|---|---|---|
| 060429 | 9/1982 | European Pat. Off. |
| 085182 | 8/1983 | European Pat. Off. |
| 0282778A | 3/1987 | European Pat. Off. |
| 277631 | 8/1988 | European Pat. Off. |

*Primary Examiner*—David B. Springer
*Attorney, Agent, or Firm*—Keil & Weinkauf

[57] ABSTRACT

Purification of 7-chloroquinoline-8-carboxylic acids I

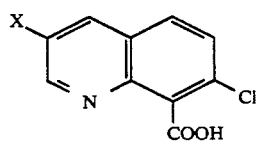

(X=H, halogen, lower alkyl group) by recrystallization from lower alcohols which are miscible with water, by carrying the recrystallization in the presence of small amounts of a base.

The quinolinecarboxylic acids I are valuable crop protection agents.

6 Claims, No Drawings

PROCESS FOR THE PURIFICATION OF 7-CHLOROQUINOLINE-8-CARBOXYLIC ACIDS

The present invention relates to an improved process for purifying 7-chloroquinoline-8-carboxylic acids of the general formula I

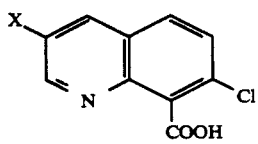

in which X denotes hydrogen, halogen or a lower alkyl group.

It is generally known (for example EP-A 085 182, EP-A 277 631 and EP-A 282 778) that the compounds of type I which are used as active ingredients in the crop protection sector can be prepared by oxidation of corresponding 8-methyl, 8-halogenomethyl or 8-dihalogeno-methyl compounds with nitric acid. The crude products which are moist with water are normally purified by recrystallization from lower alcohols such as methanol, isopropanol (EP-A 277 631, EP-A 282 778) or methyl glycol (EP-A 060 429).

However, the disadvantage of these purification processes is that the quinolinecarboxylic acids are partially esterified by the alcoholic solvent, which may lead to losses of up to about 10% of carboxylic acid.

Hence the object of the invention was to remedy this deficiency.

Accordingly, a process for purifying 7-chloroquinoline -8-carboxylic acids of the formula I has been found and is characterized in that the recrystallization is carried out in the presence of small amounts of a base.

Suitable bases are primarily the alkali metal and alkaline earth metal hydroxides, but also suitable are the alkali metal and alkaline earth metal salts of weak acids, for example carbonic acid and acetic acid, as well as high-boiling tertiary amines such as triisobutylamine.

Among the alkali metal and alkaline earth metal hydroxides, particularly preferred are the alkali metal hydroxides, especially sodium and potassium hydroxide.

The base can be employed in solid form or as aqueous solution.

It generally suffices to employ 0.1 to 1% by weight, in particular 0.2 to 0.6% by weight of base, based on the quinolinecarboxylic acid which is to be purified (is moist with water).

Suitable solvents for the recrystallization are predominantly lower alcohols which are miscible with water and have up to 4 C atoms, including, for example, alkanols such as methanol, ethanol, isopropanol and alkoxyalkanols such as methyl glycol and, especially, 1-methoxy-2-propanol.

The amount of the solvent used should be such that the quinolinecarboxylic acid (crude substance) to be purified completely dissolves on heating. It is often advisable to use twice to 10 times the amount of solvent, based on the weight of the crude substance I which is moist with water.

When 1-methoxy-2-propanol is used as solvent, generally about 2 to 6 times the amount, based on the weight of the crude substance I which is moist with water, is required.

Apart from the improvement according to the invention, the recrystallization is carried out as usual by dissolving the quinolinecarboxylic acid I which is moist with water and is to be purified, together with the mineral base, by strongly heating and stirring in the alcoholic solvent, and then allowing the solution to cool slowly to about 20° to 25° C. A linear cooling gradient of about 10° to 20° C./h is advisable to achieve slow crystal growth and thus high purity of the crystalline final products. The crystalline quinolinecarboxylic acid which is deposited is separated off in a conventional manner, for example by filtration or centrifugation, and can subsequently be washed free of surface contaminants from the mother liquor using small amounts of fresh, possibly ice-cooled solvent. A particularly expedient embodiment comprises dissolving the crude substance I which is to be purified at temperatures above 100° C. If a solvent which boils below this temperature is used, the process is carried out in a closed vessel under the autogenous pressure of the solution—at about 3 or 4 bar. The method is particularly advisable in the case of 2-methoxy -2-propanol as solvent. In this case it is advantageous to dissolve the crude substance at a temperature of 130° to 170° C.

The improved process according to the invention can be applied successfully to all quinolinecarboxylic acids I complying with the definition, especially to those compounds in which X has the following meaning
hydrogen;
halogen, preferably fluorine, chlorine and bromine, especially chlorine or
$C_1$–$C_4$-alkyl such as methyl, ethyl, propyl, isopropyl, butyl, sec.-butyl and tert.-butyl, preferably methyl.

The undesired impurities in the crude substances mainly result from the formation of by-products both in the chlorination of the 8-methylquinolinecarboxylic acid which is used as starting substance, on the ring system and on the methyl group, and in the subsequent oxidation of these compounds to the quinoline-8-carboxylic acids.

The water content, owing to the preparation, of the 7-chloroquinoline-8-carboxylic acids to be purified is generally between 1 and 50%.

The 7-chloroquinoline-8-carboxylic acids to be purified with higher yields by the process according to the invention are used, for example, as crop protection agents.

EXAMPLES

A suspension of, in each case 100 g of an impure 7-chloroquinoline-8-carboxylic acid I which is moist with water (crude product) in 400 of 1-methoxy-2-propanol was mixed with 1 g of 50% strength aqueous sodium hydroxide solution and heated in a closed apparatus to 150 ° C., resulting in an elevated pressure of about 3.1 bar. After the carboxylic acid had completely dissolved, cooling was allowed to take place over the course of about 7 hours to about 25° C., and subsequently the product which had crystallized out was filtered off. It was then washed with 100 ml of solvent and dried.

For comparison, these recrystallizations were repeated under identical conditions but without addition of a base.

The purity of the recrystallized product was about 97 to 98% in each case.

The following table shows that the loss of required product from quinolinecarboxylic acids I with various contents of water and impurities (= crude product CP)

is considerably less when alkali metal hydroxide is added. The meanings in the table are:

W the water content of the crude product CP
DP the dried crude product not including water
I/DP the proportion of quinolinecarboxylic acid I in the dried crude product DP (not including water).

TABLE

Loss of quinolinecarboxylic acid I on recrystallization from 1-methoxy-2-propanol with and without addition of sodium hydroxide solution.

| Ex. | X | W (% by wt.) | I/DP (% by wt.) | Loss of I in the recrystallization [% by wt.] | |
|---|---|---|---|---|---|
| | | | | with NaOH | without NaOH |
| 1 | Cl | 39 | 76 | 12 | 24 |
| 2 | Cl | 32 | 81 | 12 | 24 |
| 3 | Cl | 31 | 83 | 9 | 19 |
| 4 | Cl | 24 | 66 | 12 | 20 |
| 5 | CH₃ | 30 | 77 | 13 | 18 |

We claim:

1. Process for purifying 7-chloroquinoline-8-carboxylic acids of the general formula I

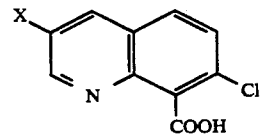

in which X denotes hydrogen, halogen or a lower alkyl group, by recrystallization from lower alcohols which are miscible with water, characterized in that the recrystallization is carried out in the presence of small amounts of a base.

2. Process according to claim 1, characterized in that an alkali metal or alkaline earth metal hydroxide is used as base.

3. Process according to claim 1 characterized in that 1-methoxy-2-propanol is used as solvent.

4. Process according to claim 3, characterized in that the quinolinecarboxylic acids to be recrystallized are dissolved at 130° to 170° C. under the autogenous pressure of the system.

5. Process according to claim 1 characterized in that 0.1 to 1% by weight of base, based on the 7-chloro-8-quinolinecarboxylic acid to be purified, is used.

6. The process of claim 1 wherein the lower alcohol is methanol, ethanol or isopropanol, and the lower alkoxyalkanols are methyl glycol and 1-methoxy-2-propanol.

* * * * *